United States Patent [19]

Marcus et al.

[11] Patent Number: 5,182,104

[45] Date of Patent: Jan. 26, 1993

[54] TOPICAL VIRUCIDAL COMPOSITION FOR TREATMENT OF MUCOCUTANEOUS TISSUE

[76] Inventors: Stanley Marcus, 1400 E. Federal Way, Salt Lake City, Utah 84102; Wendy Y. Kim, 968 E. Green Oaks Dr., Bountiful, Utah 84010

[21] Appl. No.: 730,612

[22] Filed: Jul. 16, 1991

[51] Int. Cl.$^5$ .................... A01N 31/14; A61K 31/075
[52] U.S. Cl. .................................. 424/78.07; 424/405; 514/887; 514/717
[58] Field of Search ........................ 424/405, 78.07, 78

[56] References Cited

U.S. PATENT DOCUMENTS

| | | | |
|---|---|---|---|
| 4,201,235 | 5/1980 | Ciavatta | 137/7 |
| 4,670,471 | 6/1987 | Clark | 514/724 |
| 4,883,659 | 11/1989 | Goodman et al. | 424/78 |

OTHER PUBLICATIONS

Koop, C. Everett, M.D., ScD, Surgeon General, Oct. 16, 1987, 258JAMA2111.

*Primary Examiner*—Thurman K. Page
*Assistant Examiner*—Neil Levy

[57] ABSTRACT

This invention pertains to a topically applied composition with a virucidal impact on mucocutaneous tissue. Ingredients essential to the efficacy of the formulated combination include a polyethylene glycol polymer known as Nonoxynol-9("N-9")in admixture with selected fat soluble vitamins A, D and E in the form of vegetable oil (and) retynyl palmitate (and) ergocalciferol together with tocopherol acetate. The invention is directed particularly to inactivation of herpes virus and human papilloma virus as manifested in cold sores, lesions, fever blisters, canker sores and warts. The N-9 contains viral activity while the vitamins effect restoration and strengthening of the damaged tissue cells.

8 Claims, No Drawings

TOPICAL VIRUCIDAL COMPOSITION FOR TREATMENT OF MUCOCUTANEOUS TISSUE

BACKGROUND

1. The Field of the Invention

This invention relates to an improved anti-microbial agent. More particularly, this invention is specifically directed to an additive for water-based polymerized compositions and provides an ethylene glycol-based composition for topical anti-viral treatment of mucocutaneous tissue.

2. The Background Art

Ethylene glycol, an inexpensively available organic chemical, is readily polymerized. Polyethylene glycol (PEG) is widely used in our society. A PEG polymer with the molecular weight of 968, commonly referred to as nonoxynol-9 or N-9, is a viscous liquid that has long been used as a lubricant and spermicide in concentrations of 2%-5% in over-the-counter (OTC) preparations, e.g., Ortho-creme, Gentersal, Delfen. Products known commercially as ViroNox-9 and aidsPLUS+ marketed by MicroBio Products, Inc. of Tempe, Ariz. and Medical Diagnostic Technologies, Inc. dba MeDi-Tech of Ventura, Calif. respectively, though directed toward cleansing of body surfaces based on other active ingredients, also contain N-9 in concentrations of approximately 2% and are known to provide additional protection against microbiological contamination. The safety, absence of toxicity and freedom from any harmful side effects of these preparations is attested to by long, continued and repeated use.

The spermicide N-9 has been shown to be virucidal and to reduce the frequency of infections due to both viral and bacterial sexually transmitted diseases. It has been suggested that this anti-viral action of N-9 may be the reason why women who use spermicides are far less likely to have cervical cancer in view of the fact that a leading cause of cervical cancer is almost undoubtedly herpes virus. A recent review of scientific archival reports by B. North in *Journal of Reproductive Medicine*, 33:307, 1988, concludes that the advice of former U.S. Surgeon General Everett Koop be followed for widespread use of N-9 in contraceptive devices as an aid in reducing risk from bacterial and viral infection passed by sexual intercourse. Of course, this includes herpes infection.

For critical evaluations or comparison considerations of prophylactic substances to be used against an infectious disease agent it is necessary to have certain basic information; for example, the infectiousness of the agent, the extent of the disease in the population under test, the extent and significance of latency of the disease to treatment. In these regards, among diseases of great infectiousness, the virus disease herpes is an example. Other virus diseases of great infectiousness which we have overcome by immunization are smallpox, measles and poliomyelitis. To date, no effective immunization against herpes has been developed. Major reasons for this failure may include the facts that initial infections with herpes are usually mild or inapparent, that the disease becomes latent (i.e., occult or inapparent, present but inactive), and that the disease is widespread.

The mildness of the usual infection or recurrences may not offer a significant public health hazard but such recurrences are of major social significance whether of oral or genital appearance.

The widespread nature of the disease is well understood. Critical estimates of the extent of the disease is well documented. Critical estimates of the extent of the disease are based on serologic test and postmortem evidence. Serologic testing shows that more than 90% of adults have been infected with herpes, according to Rivers and Horsfall in *Viral and Rickettsial Infections of Man*, 3rd ed., p. 778.

Although the mechanism of herpes latency remains unknown, the evidence is strong that the virus remains latent, after primary infection, in neural tissue. Reactivation from latency involves return of virus through nerve tissue to peripheral cutaneous cells. As is so obvious, the cells of the mucocutaneous oral region are a preferred site for boisterous growth of the virus. The herpes virus is readily cultured from the lesions.

Virus is found free in blister fluid and tissue in herpetic lesions. It is apparent that the virus enters, reproduces and destroys new cutaneous cells that it encounters. It follows that stopping the passage of virus from neural cells or infected cutaneous cells to uninfected cells will block the progress of a lesion and so result in more rapid healing.

BRIEF SUMMARY OF THE INVENTION

It has been found that N-9 accomplishes the task of counteracting the potential for viral infection and of topically treating herpes viral infections, and these benefits can be enhanced by incorporating N-9 in admixture with certain vitamins. A synergism of benefit is achieved when N-9 is used in combination with vitamins such as vitamins A, D and E with their regenerative and healing effect on dermal tissue. For example, it has been shown that a simple preparation of N-9 inactivates free virus thereby preventing reinfection and that the topical application results in direct and immediate virucidal effect. Further, the healing and soothing effects of these vitamins when topically applied to lesions is accompanied by a reduction in localized tissue edema, a replacement of destroyed cells and a healing of damaged cells. Accordingly, this application of N-9, when combined with the nourishing and regenerative functions performed by topical application of selected vitamins, results in a commensurate benefit which is greater than the sum of the benefits of N-9 and vitamin admixtures when used individually, due in part to the simultaneous, reciprocal acceleration of the respective functions of the various ingredients.

Some clinical reports are to the effect that N-9 alone accomplishes remission of certain diseases only with the added presence of one of the drugs for which efficacy has been claimed, e.g., interferon alpha. This and similar studies are open to the criticism that N-9 alone was not studied and that the clinical disease was well developed when therapy was begun.

Just as penicillin is valueless against far advanced and well established pneumococcal pneumonia, the efficacy of N-9 is not as readily evident when applied to a well established cold sore.

Not all surfactant substances are virucidal in useable concentrations and some, e.g., Tween-20 and Tween-80, interfere with the virucidal action of N-9.

OBJECTS OF THE INVENTION

In view of the foregoing, it is a primary object of the present invention to provide novel, nontoxic, improved means for reducing the probability of microbiological, in particular viral, infection of humans upon exposure to such microorganisms.

It is also an object of the present invention to reduce the cost of manufacturing a product capable of providing this singularly beneficial anti-viral effect.

Consistent with the foregoing objects, and in accordance with the invention as embodied and broadly described herein, a novel, topical antimicrobial agent is disclosed in one embodiment of the present invention as a polyethylene glycol surfactant which inactivates viral microorganisms upon contact, in combination with tissue regenerative and revitalizing additives.

As set out further below, this invention provides, with improved simplicity and benefit and reduced cost, a considerably less painful, less invasive, more easily applied and less restrictive composition for topical treatment of viral herpes infections. This invention is particularly well suited to use in connection with herpes lesions, fever blisters, cold sores, and canker sores by application of the combination of components in liquid form directly to the surface of various cutaneous parts of the body, in particular mucocutaneous tissues, i.e., lips and surrounding areas. This invention may also advantageously be used in other applications requiring the topical application of virucidal compositions, such as, for example, with respect to human papilloma virus (HPV), i.e., warts.

The foregoing and other objects and features of the present invention will become more fully apparent from the following description taken in conjunction with the appended claims. Understanding that this description depicts only a typical embodiment of the invention and is, therefore, not to be considered limiting of its scope, the invention will be described with additional specificity and detail through use of the accompanying description.

DETAILED DESCRIPTION OF THE PREFERRED EMBODIMENT

It will be readily understood that the components of the present invention, as generally described and illustrated herein, could be arranged and designed in a wide variety of different configuration and permutations of composition. Thus, the following more detailed description of the embodiments of the system and method of the present invention, as represented in the following description, is not intended to limit the scope of the invention, as claimed, but it is merely representative of the presently preferred embodiment of the invention.

One presently preferred formula for the subject invention is as follows:

| CTFA Name | Percent Ranges | Weight % |
| --- | --- | --- |
| Snow White Petrolatum | 28.0–50.0 | 47.0 |
| Nonoxynol 9 | 2.0–5.0 | 2.0 |
| PPG-5 Lanolin Wax | 2.0–5.0 | 5.0 |
| Bleached Beeswax | 0.6–1.2 | 1.1 |
| Mineral Oil | 5.0–10.0 | 9.0 |
| Methyl Paraben | 0.1–0.3 | .2 |
| Stearyl Alcohol | 2.5–5.0 | 4.8 |
| Stearic Acid | 2.8–5.0 | 4.6 |
| DI Water | 10.0–21.0 | 20.0 |
| Propyl Paraben | 0.1–0.2 | .2 |
| Triethanolamine 85% | 0.1–0.5 | .4 |
| Vegetable Oil (and) Retinyl Palmitate (and) Ergocalciferol | 0.2–1.0 | .8 |
| Tocopherol Acetate | 0.2–1.0 | .8 |
| SDA 40 | 1.0–5.0 | 4.0 |

-continued

| CTFA Name | Percent Ranges | Weight % |
| --- | --- | --- |
| | | 99.9 |

Application of N-9 and the accompanying restorative components before exposure to various viruses will help prevent occurrence of lesions from such infections. The subject additive invention is to be applied before exposure to viral infection.

To understand the efficacy of the subject invention against the different viruses which it inactivates, it is necessary to disclose the means by which these viruses gain entrance and then spread within the human host.

The herpes viruses are transmitted by contact. Most people are infected at an early age. For unexplained reasons the latent infection can be activated into overt, obvious disease. It is assumed that the activated virus grows and reproduces in the susceptible cells. When the host cell loses viability and sickens the viruses burst out into the surrounding areas. One or more mature virus organisms attach to any susceptible cell nearby, enter the cell and proceed to grow and reproduce in the new cell host. The principal mechanism whereby the subject invention stops this progression is by being available in the area, N-9 attaching to the virus particles and inactivating them while restorative additives enhance the viability of and contribute to the recuperation of the exposed tissue cells at the infected site. If the N-9 agent does not reach the area of infection by topical application it cannot be effective.

The viruses of herpes and HPV have a definite structure which includes a surface envelope containing lipid (fat) material. Some substances which react with lipids such as polyethylene glycols inactivate these viruses. These polyethylenes are also called surfactants, i.e., surface active agents. Not all such agents are active against these lipid envelope containing viruses.

It should be noted that even as not all surfactant substances effect viral inactivation, some other surfactants are active only against certain lipid envelope-containing viruses such as herpes. Accordingly, an analysis of the safety and efficacy of N-9 alone as well as such other topical surfactants with respect to virucidal use in a product similar to the subject invention is beyond the scope of this application.

From the above discussion, it will be appreciated that the present invention provides an improved composition and method for topical therapeutic and prophylactic virucidal treatment of inter alia Herpes and HPV. Moreover, since the present invention has so few and such inexpensive ingredients, compounding is greatly simplified and the cost of the manufacturing process and of the raw materials is negligible.

The present invention may be embodied in other specific forms without departing from its spirit or essential characteristics. Further objects and advantages of this invention will become apparent from a consideration of the summary and ensuing description of it. The described embodiment is to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by U.S. Letters Patent is:

1. A non-cosmetic virucidal composition for medicinally therapeutic and prophylactic topical treatment of mucocutaneous oral tissues the active ingredients of which, in combination, consist of:
   a polyethylene glycol polymer with a molecular weight of 968 present in concentrations between two and five percent by weight; and
   a combination of fat soluble vitamins present in an amount between 0.2 and one percent by weight.

2. A composition according to claim 1 wherein the polyethylene glycol polymer has a molecular structure which is substantially that of nonoxynol-9.

3. A composition according to claim 1 wherein the combination of fat soluble vitamins consists of vegetable oil and retinyl palmitate and ergocalciferol and tocopherol acetate in comparable respective amounts.

4. A non-cosmetic virucidal composition for medicinally therapeutic and prophylactic topical treatment of mucocutaneous oral tissue comprising, in combination, a mixture of polyethylene glycol polymer with a molecular weight of 968 present in concentrations of between two and five percent by weight, and a combination of fat soluble vitamins present in concentrations of between 0.2 and one percent respectively, wherein:
   the polyethylene glycol polymer has a molecular structure which equates to that of nonoxynol-9; and
   the combination of fat soluble vitamins consists of vegetable oil and retinyl palmitate and ergocalciferol and tocopherol acetate.

5. A composition according to claim 4 wherein said mixture is present in an emulsion, containing about 2.4 to about seven percent active ingredients.

6. A composition according to claim 4 wherein said mixture is present in a solid medium, containing about 2.4 to about seven percent active ingredients.

7. A composition according to claim 5 wherein said emulsion is based in a cream base or a petrolatum base or a wax base or a base combining a cream and petrolatum or a base combining a cream and a wax or a base combining a wax and petrolatum or a base combining a cream and a wax and petrolatum.

8. A composition according to claim 6 wherein said solid medium is based in a petrolatum base or a wax base or a base combining a wax and petrolatum.

* * * * *